United States Patent [19]

Yamada et al.

[11] Patent Number: 4,836,906

[45] Date of Patent: Jun. 6, 1989

[54] AIR-FUEL RATIO SENSOR

[75] Inventors: Tetsusyo Yamada; Nobuhiro Hayakawa; Kazunori Yokota, all of Aichi, Japan

[73] Assignee: NGK Spark Plug Co., Ltd., Nagoya, Japan

[21] Appl. No.: 138,531

[22] Filed: Dec. 28, 1987

[30] Foreign Application Priority Data

Dec. 27, 1986 [JP] Japan .................. 61-313374

[51] Int. Cl.$^4$ ............................................. G01N 27/58
[52] U.S. Cl. .................................. 204/410; 204/412; 204/425
[58] Field of Search .............. 204/429, 428, 425, 426, 204/1 S, 410, 412

[56] References Cited

U.S. PATENT DOCUMENTS

| 4,021,326 | 5/1977 | Pollner et al. | 204/429 |
|---|---|---|---|
| 4,151,060 | 4/1979 | Isenberg | 204/428 |
| 4,240,890 | 12/1980 | Watanabe et al. | 204/428 X |
| 4,402,820 | 9/1983 | Sano et al. | 204/425 |
| 4,476,008 | 10/1984 | Sano et al. | 204/425 |
| 4,713,166 | 12/1987 | Kojima et al. | 204/425 |
| 4,722,779 | 2/1988 | Yamada et al. | 204/410 |

FOREIGN PATENT DOCUMENTS

| 19554 | 2/1983 | Japan | 204/429 |
|---|---|---|---|
| 67454 | 4/1984 | Japan | 204/429 |

Primary Examiner—G. L. Kaplan
Attorney, Agent, or Firm—Sughrue, Mion, Zinn, Macpeak and Seas

[57] ABSTRACT

An air-fuel ratio sensor in which the temperature dependence as well as the pressure dependence of a detection signal obtained by the air-fuel ratio sensor are suppressed to thereby improve the accuracy in air-fuel ratio by the air-fuel ratio sensor, which is not influenced by deposits in an exhaust gas and which is high in durability. The suppression is achieved by using a gas-diffusion limiting portion having such critical parameters as 10–30% porosity, 1–3 micrometers mean pore size and 200–1000 micrometers thickness. Alternatively the parameters may be 15–25% porosity, 0.1–7 micrometers pore size and 400–800 micrometers thickness.

15 Claims, 7 Drawing Sheets

AIR-FUEL RATIO SENSOR

BACKGROUND OF THE INVENTION

This invention relates to an air-fuel ratio sensor for detecting an air-fuel ratio of an air-fuel mixture to be supplied to a variety of combustion equipment such as an internal combustion engine or the like on the basis of oxygen concentration in an exhaust gas.

Conventionally, an air-fuel ratio sensor of the kind as described above, uses a detection element in which a pair of porous electrodes are respectively laminated on opposite surfaces of a solid electrolyte having oxygen-ion conductivity.

Such an air-fuel ratio sensor is called a diffusion limited current type as disclosed, for example in Japanese Patent Unexamined Publication No. 57-48648/1982, Japanese Utility Model Unexamined Publication No. 60-17452/1985. In the diffusion limited current type gas sensor a porous gas-diffusion limiting layer, for limiting diffusion of a measuring gas is formed on one of the porous electrode surfaces of the foregoing detection element either directly or through a closed space. The electrode at the gas-diffusion limiting layer side is used as a cathode, and a predetermined voltage is applied between the electrodes so as to detect an air-fuel ratio on the basis of a diffusion limited current flowing at this time. Further, there has been an air-fuel ratio sensor as disclosed, for example, in Japanese Patent Unexamined Publication No. 59-178354/1984, in which two detection elements, each arranged in the same manner as described above, are disposed so as to cause the respective porous electrodes thereof to contact with a measuring gas chamber in which diffusion of a measuring gas is limited by a gas-diffusion limiting layer. One of the detection elements acts as an oxygen pumping element while the other detection element acts as an oxygen concentration cell element so that an air-fuel ratio is detected on the basis of a current flowing in the oxygen pumping element or a voltage generated between the electrodes at the opposite ends of the oxygen concentration cell element.

In the foregoing detection elements, however, the current flowing when a predetermined voltage is applied between the porous electrodes when a predetermined current is flowed through the porous electrodes, or the voltage generated between the porous electrodes, may vary depending on the temperature when the detection elements are in use. Therefore, there has been a problem in that in order to obtain a stable detection signal by using the foregoing air-fuel ratio sensor, it is necessary to maintain the detection elements at a predetermined temperature.

Various efforts have been made to solve the problem of the temperature dependence of the detection signal of the air-fuel ratio sensor of the kind described above to thereby enlarge the range of the temperatures at which the air-fuel ratio sensor can be used. For example, as disclosed in Japanese Patent Unexamined Publication No. 59-67454/1984, the pore size of the gas-diffusion limiting layer formed on the detection element on one of the porous electrodes was set to 300 Å–400 Å.

When the thus arranged air-fuel ratio sensor was attached to actual combustion equipment (for example, an internal combustion engine) and operated, the detection signal varied as the pressure in the exhaust system fluctuated so that no stable detection signal could be obtained, even though the exhaust gas temperature remained stable. That is, in combustion equipment, not only the exhaust gas temperature, but also the exhaust gas pressure, vary depending on the running state of the combustion equipment. Therefore, no stable detection signal can be obtained even if the problem of the temperature dependence of the detection signal could be solved as described above.

When the gas-diffusion limiting layer having a pore size of 300 Å–400 Å is used as described above, a rate of molecular diffusion is reduced when a measuring gas passes through the gas-diffusion limiting layer. That is, when the gas-diffusion limiting layer is formed on one of the porous electrodes and a predetermined voltage is applied between the electrodes, with the one electrode as a cathode, a current I flowing in the detection element can be represented by the following expression (1):

$$I \alpha 4 \cdot F \cdot S \cdot Dg \cdot Pg / R \cdot T \cdot L \tag{1}$$

where F represents Faraday constant, R a gas constant, S a sectional area of the diffusion pore of the gas-diffusion limiting layer, T an absolute temperature, L a thickness of the gas-diffusion limiting layer, Pg the partial pressure of oxygen gas in the measuring gas, and Dg a diffusion coefficient of the measuring gas.

Further, diffusion of the measuring gas is divided into molecular diffusion represented by a diffusion coefficient Dm shown by the following expression (2), and fine pore diffusion (Knudsen diffusion) represented by a diffusion coefficient Dk shown by the following expression (3):

$$Dm \alpha T^{1.75} \cdot Pa^{-1} \tag{2}$$

where Pa represents the total pressure of the measuring gas atmosphere; and $$Dk \alpha r \cdot T^{0.5} \cdot M^{-0.5} \tag{3}$$

where r represents the mean pore size and M the molecular weight of the measuring gas.

When the measuring gas passes through the gas-diffusion limiting layer only by molecular diffusion, the current I flowing in the detection element is represented by the following expression (4):

$$I \alpha T^{0.75} \cdot S / L \tag{4}$$

where Pg α Pa.

When the measuring gas passes through the gas-diffusion limiting layer only by fine pore diffusion, the current I flowing in the detection element is represented by the following expression (5):

$$I \alpha T^{-0.5} \cdot Pg \cdot S / L \tag{5}$$

Accordingly, the current I actually flowing in the detection element can be represented by the following composite expression (6) of the foregoing expression (4) and (5):

$$I \alpha (K1 \cdot T^{0.75} \cdot S / L + K2 \cdot T^{-0.5} \cdot Pg \cdot S / L) \tag{6}$$

where K1 and K2 represent coefficients and K1+K2=1.

Therefore when the air-fuel ratio sensor is formed by using the gas-diffusion limiting layer having a pore size of 300 Å–400 Å, the rate of the fine pore diffusion represented by the foregoing expression (5) becomes large, so that the detection signal is influenced by the oxygen partial pressure Pg in the measuring gas which varies in proportion to the measuring gas atmosphere total pressure (exhaust gas system pressure) Pa.

Further, in order to solve the problem of pressure dependence of the detection signal, the pore size of the gas-diffusion limiting layer may be made large to thereby increase the rate of the molecular diffusion represented by the foregoing expression (4). If merely the pore size of the gas-diffusion limiting layer is made large, however, there have been such problems that not only the temperature dependence of the detection signal becomes large but also deposits such as Pb, P, S, and the like, which are contained in an exhaust gas and which are harmful to an electrode material, are transmitted through the gas-diffusion limiting layer.

SUMMARY OF THE INVENTION

It is therefore an object of the present invention to provide an air-fuel ratio sensor in which the temperature dependence as well as the pressure dependence of detection signal obtained by the foregoing air-fuel ratio sensor are suppressed to thereby improve the accuracy in air-fuel ratio detection by the air-fuel ratio sensor, which is not influenced by deposits in an exhaust gas and which is high in durability.

In order to attain the above object, according to the present invention, in the air-fuel ratio sensor, comprising a detection element in which a pair of porous electrodes are laminated respectively on opposite surfaces of a solid electrolyte having oxygen-ion conductivity, and a gas-diffusion limiting layer provided on one of the porous electrodes of the detection element directly or indirectly through a closed space so as to limit diffusion of a measuring gas flowing into the one porous electrode, the gas-diffusion limiting layer is constituted by a porous layer having porosity of 10%–30%, a mean pore size of 1 $\mu$m–3 $\mu$m, and a thickness of 200 $\mu$m–1000 $\mu$m.

Here, the air-fuel ratio sensor, according to the present invention, is arranged such that the gas-diffusion limiting layer is formed on the detection element on one of the porous electrodes directly or indirectly through a closed space. Specifically, the air-fuel ratio sensor according to the present invention includes: an air-fuel ratio sensor of the threshold current type in which a predetermined voltage is applied between porous electrodes of a detection element and oxygen concentration of a measuring gas (that is, an exhaust gas) is detected on the basis of a corresponding current: an air-fuel ratio sensor of the type in which two detection elements are disposed in opposition to each other through a measuring gas chamber acting as a closed space, in which one of the detection elements and the other detection element are caused to act as an oxygen pumping element and an oxygen concentration cell element, respectively, so that oxygen concentration of a measuring gas is detected on the basis of a current flowing in the oxygen pumping element or a voltage generated in the oxygen concentration cell element; and so on.

Further, the air-fuel ratio sensor of the type in which an air-fuel ratio is detected by using two detection elements as described above may include: an air-fuel ratio sensor in which an atmosphere lead-in chamber into which the atmosphere is directed is formed at the porous electrode side, opposite to the measuring gas chamber side of the detection element which is used as an oxygen concentration cell element so as to obtain a detection signal which varies not only in a lean region of the air-fuel ratio but varies continuously, extending from a lean region to a rich region of the air-fuel ratio; an air-fuel ratio sensor in which an inner oxygen reference source communicated with the outside, or a measuring gas chamber, is formed at the foregoing electrode side through a leakage resistant portion for leaking oxygen; and so on. The present invention is applicable to the air-fuel ratio sensors of the type as described above.

As the solid electrolyte of oxygen-ion conductivity constituting the detection element, typically, a solid solution of zirconia and yttria, zirconia and calcia, or the like may be used. In addition to the foregoing materials, a solid solution of cerium dioxide, sodium dioxide, hafnium dioxide, a solid solution of a perovskite type oxide, a solid solution of three-valancy metal oxide, or the like can be used.

As the porous electrodes laminated on the opposite surfaces of the solid electrolyte, platinum, rhodium, or the like, having a catalysts of oxidation reaction, may be used. Examples of the method of forming the porous electrode include a method in which the powder of the method of forming the porous electrode include a method in which the powder of the metal described above is mixed, as a main component, with powder of the same ceramic material as that constituting the solid electrolyte so as to form paste. The paste is thick-film-printed on the opposite surfaces of the solid electrolyte and then sintered, a method using a thin-film technique such as flame coating, chemical plating, or evaporation, and so on.

In the case where the porous electrode at the opposite side to the gas-diffusion limiting layer side is in direct contact with a measuring gas, that is, an exhaust gas, it is preferable to form a porous protecting layer of alumina, spinel, zirconia, mullite, or the like, on the surface of this electrode.

Next, the gas-diffusion limiting layer is provided for limiting diffusion of the measuring gas flowing into the porous electrode at the gas-diffusion limiting layer side. The gas-diffusion limiting layer may be formed of alumina, spinel, forsterite, zirconia, or the like, by using the same method as that of formation of the porous electrode.

According to the present invention, the gas-diffusion limiting layer is selected to have a porosity of 10%–30%, a mean pore size of 1 $\mu$m–3 $\mu$m, and a thickness of 200 $\mu$m–1000 $\mu$m.

A first reason why such a gas-diffusion limiting layer as selected above is used is as follows. Both the temperature dependence and the pressure dependence of the detection signal, determined by the ratio of the molecular diffusion to the fine pore diffusion when a measuring gas passes through the gas-diffusion limiting layer, are made less than a predetermined level so that a stable detection signal can be obtained even when a measuring gas temperature (that is an exhaust gas temperature) or measuring gas pressure (that is, exhaust gas pressure) varies.

That is, where the measuring gas moves in the gas-diffusion limiting layer only by the molecular diffusion represented by the foregoing expression (4), the detection signal varies by +7.6% as indicated by a solid line in FIG. 7 when the detection element temperature varies, for example, from 700° C. to 800° C., while the detection signal does not vary as indicated by a solid line in FIG. 8 even when the measuring gas pressure varies from 1.0 atm to 1.3 atm. In contrast, where a measuring gas moves in the gas-diffusion limiting layer only by the fine pore diffusion represented by the foregoing expression (5), the detection signal varies by −4.8% as indicated by a one-dotted chain line in FIG. 7 when the detection element temperature varies, for example, from 700° C. to 800° C., while the detection signal varies by +30% as indicated by one-dotted chain line in FIG. 8 when the measuring gas pressure varies from 1.0 atm to 1.3 atm. Therefore, according to the present invention, in order to make a fluctuation width of the detection signal be within 10% to stably detect an air-fuel ratio, the gas-diffusion limitation layer is selected to be as described above.

Further, if the gas-diffusion limiting layer is selected to be as described above, the ratio of the molecular diffusion to the fine pore diffusion, when the measuring gas moves in the inside of the gas-diffusion limiting layer is made to be about 1:0–2:1. Therefore, the fluctuation width of the detection signal against the foregoing change in temperature is suppressed to be within a range of from 3.5% to 7.6%, as indicated by slanting lines in FIG. 7, and the fluctuation width of the detection signal against the foregoing change in pressure is suppressed to be within a range of from 0% to 10%, as indicated by slanting lines in FIG. 8.

A second reason why the gas-diffusion limiting layer is selected to be as described above is to improve the durability of the air-fuel ratio sensor. That is, to suppress the fluctuation of the detection signal to be within 10%, due to the change in temperature and the change in pressure, even if the movement of the measuring gas in the gas-diffusion limiting layer is made to be performed only by the molecular diffusion as described above, it is necessary to enlarge the pore size and the porosity. Even if the pore size and the porosity are merely made large, however, deposits contained in the measuring gas harmful to the porous electrode pass through the gas-diffusion limiting layer when the measuring gas, per se, passes through the gas-diffusion limiting layer. Therefore, if the gas-diffusion limiting layer is selected to be as described above, it is possible to prevent the deposits in the measuring gas from transmitting through the gas-diffusion limiting layer to flow into the porous electrode, so that deterioration of the porous electrode is suppressed to thereby improve durability of the air-fuel ratio sensor.

In order to further reduce the temperature dependence and pressure dependence of the election signal while making sure of the durability of the air-fuel ratio sensor, it is preferable to range the porosity, the thickness and the pore size to be within 20±5%, 600±200 $\mu$m, and 0.1 $\mu$m–7 $\mu$m, respectively.

In the thus arranged air-fuel ratio sensor according to the present invention, the diffusion of the measuring gas flowing into the detection element is limited by the gas-diffusion limiting layer. Further, the measuring gas moves in the gas-diffusion limiting layer mainly by the molecular diffusion. As a result, both the temperature dependence and the pressure dependence of the detection signal obtained by the air-fuel ratio sensor according to the present invention are suppressed, so that a stable detection signal is obtained by the air-fuel ratio of which is to be detected. Further, the gas-diffusion limiting layer is selected so that the pore size thereof is not so excessively large and the thickness thereof is suitable, so that the porous electrode at the gas-diffusion limiting layer side can be protected from the measuring gas without deteriorating response.

DETAILED DESCRIPTION OF THE INVENTION

An embodiment of the present invention will be described hereunder with reference to the accompanying drawings.

Figure 1:
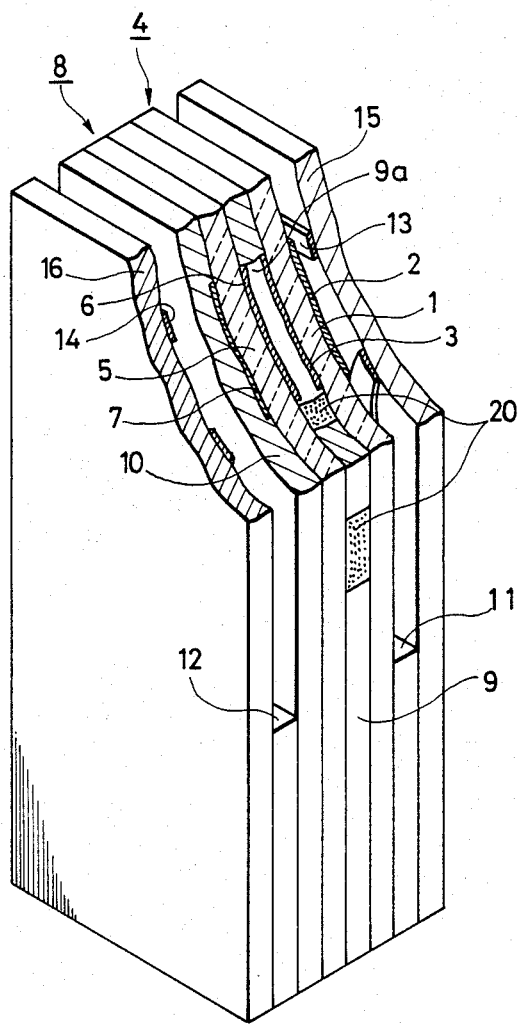
FIG. 1 is a partially cut-away perspective view showing an embodiment of the air-fuel ratio sensor according to the present invention.
Figure 2:
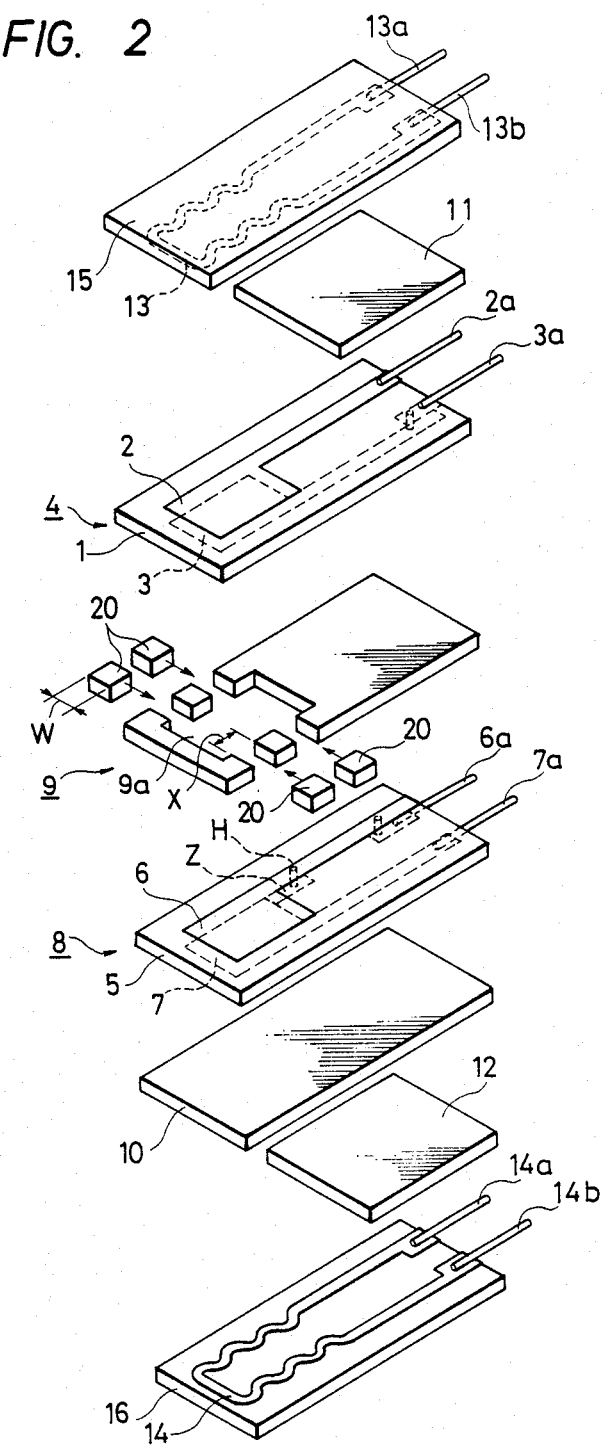
FIG. 2 is an exploded perspective view showing the air-fuel ratio sensor of the same embodiment.

First, FIGS. 1 and 2 show the arrangement of an embodiment of the air-fuel ratio sensor according to the present invention, FIGS. 1 and 2 being a partially cut-away perspective view and an exploded perspective view, respectively.

As shown in the drawings, the air-fuel ratio sensor of this embodiment is constituted by oxygen pumping element 4 in which porous electrodes 2 and 3 are laminated respectively on opposite surfaces of a solid electrolytic plate 1, an oxygen concentration cell element 8 in which porous electrodes 6 and 7 are laminated respectively on opposite surfaces of a solid electrolytic plate 5, a spacer 9 interposed between those detecting elements 4 and 8 and having a hollow portion 9a formed by the porous electrodes 3 and 6 of the detecting elements 4 and 8 disposed in opposition to each other, and a shield 10 laminated on the oxygen concentration cell element 8 at the porous electrode 7 side. Further, heating elements 15 and 16 are formed on outer side surfaces of the oxygen pumping element 4 and shield 10 through spacers 11 and 12 respectively, the heating elements 15 and 16 being provided at their surfaces opposite to the foregoing outer side surfaces with heating resistor patterns 13 and 14 respectively, so that the oxygen pumping element 4 and the oxygen concentration cell element 8 can be heated through gaps formed by the spacers 11 and 12 respectively.

The spacer 9 has a hollow portion 9a which provides a measuring gas chamber for limiting diffusion of a measuring gas between the porous electrodes 3 and 6. In the spacer 9, notches are formed in four portions of the periphery of the hollow portion 9a so as to lead a surrounding measuring gas into the hollow portion 9a, and gas-diffusion limiting layers 20 are correspondingly formed in the notch portions so as to limit diffusion of the measuring gas to be led into the inside of the hollow portion 9a.

The shield 10 is provided to shield the porous electrode 7 of the oxygen concentration cell element 8 from an outer measuring gas so as to make the electrode 7 act as an inner oxygen reference source.

That is, if an arrangement is made such that a predetermined current is caused to flow in the oxygen concentration cell element 8 to thereby pump oxygen out of the hollow portion 9a to the porous electrode 7 side as described above and the thus pumped-out oxygen is allowed to leak outside by a predetermined quantity, oxygen gas partial pressure of the porous electrode 7 is made substantially fixed so that a voltage corresponding to the oxygen partial pressure in the hollow portion 9a is generated between the electrodes 6 and 7 of the oxygen concentration cell element 8. Accordingly, being shielded from the outside by the shield 10, the porous electrode 7 is made to act as an inner oxygen reference source.

Further, to cause the porous electrode 7 to act as an inner oxygen reference source, it is necessary to make oxygen in the porous electrode 7 leak outside. In this embodiment, therefore, the porous electrodes 7 and 6 are connected to each other through porous insulator 2 of alumina or the like and a through hole H so as to allow the oxygen to leak from the porous electrode 7 into the hollow portion 9a through the porous insulator Z and the through hole H.

The thus arranged air-fuel ratio sensor of the embodiment is operated in a manner so that a predetermined voltage is applied to the heating resistor patterns 13 and 14 of the heating elements 15 and 16, respectively, through terminals 13a and 13b and terminals 14a and 14b to thereby activate the oxygen pumping element 4 and the oxygen concentration cell element 8 by heating them respectively. The porous electrodes 2 and 3 of the oxygen pumping element 4 and the porous electrodes 6 and 7 of the oxygen concentration cell element 8 are connected to such an air-fuel ratio detecting circuit 30 as shown in FIG. 3 through terminals 2a and 3a and 6a and 7a respectively, so as to drive the air-fuel ratio detecting circuit 30.

Figure 3:
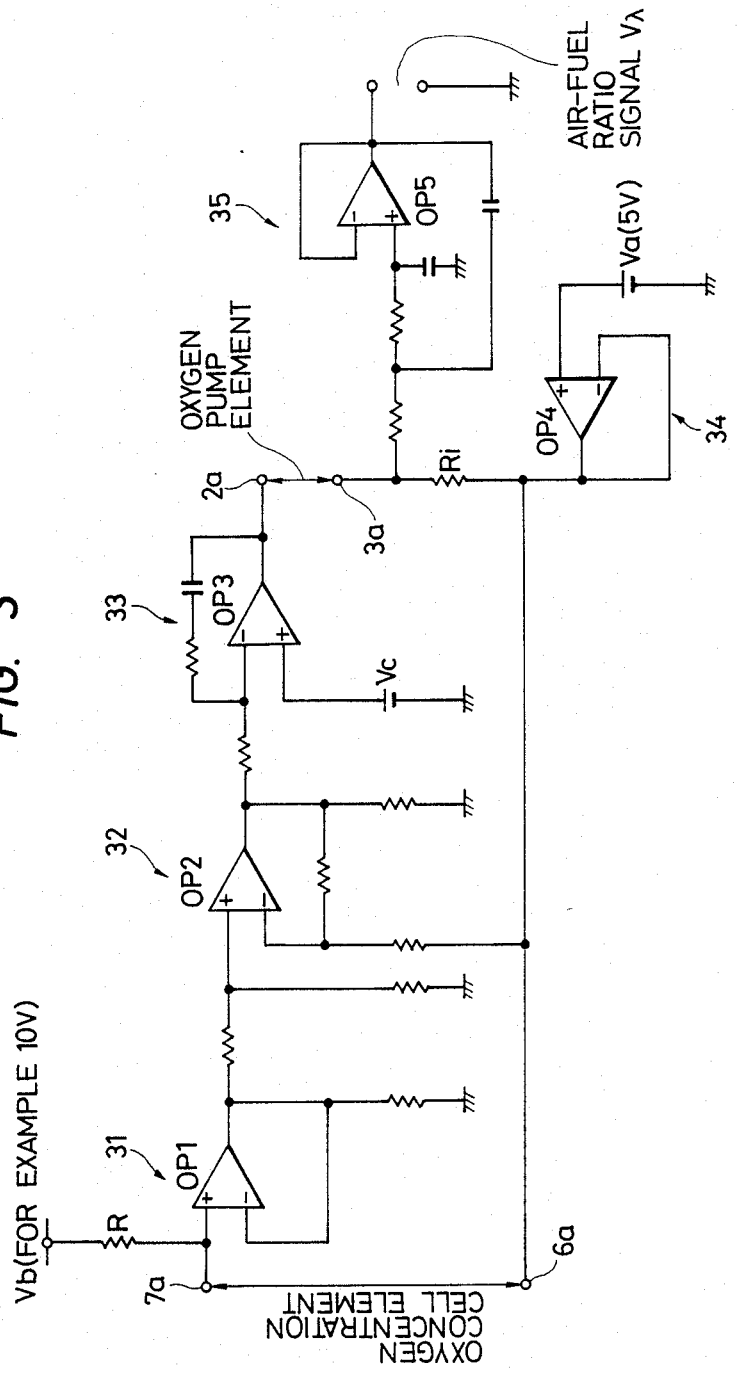
FIG. 3 is an electric circuit diagram showing the air-fuel ratio detecting circuit for actuating the air-fuel ratio sensor according to the present invention to detect an air-fuel ratio.

As shown in FIG. 3, the air-fuel ratio detecting circuit 30 is constituted by a resistor R for applying a predetermine voltage Vb (for example, 10 V) to the porous electrode 7 of the oxygen concentration cell element 8 so as to limit a current flowing into the other porous electrode 6 to which a reference voltage Va (for example, 5 V) is applied; a buffer circuit 31 constituted by an operational amplifier OP1 for detecting a voltage which is generated between the opposite electrodes of the oxygen concentration cell element 8 and made high by the reference voltage Va; a non-inverted amplifying circuit 32 constituted by an operational amplifier OP2 for amplifying a detection voltage produced from the buffer circuit 31; a comparing and integrating circuit 33 constituted by an operational amplifier OP3 for comparing the detection voltage amplified by the non-inverted amplifying circuit 32 with a predetermined reference voltage Vc so as to produce a control voltage which gradually decreases with a predetermined integral constant when the detection voltage is larger than the reference voltage Vc and which gradually increases with a predetermined integral constant when the detection voltage is smaller than the reference Voltage Vc; a buffer circuit 34 constituted by an operational amplifier OP4 for producing the foregoing reference voltage Va; a current detecting resistor Ri for applying the reference voltage Va from the buffer circuit 34 to the porous electrode 3 of the oxygen pumping element 4 at the hollow portion 9a side so as to detect a current flowing between the porous electrode 3 and the other porous electrode 2 to which a controlling voltage from the comparing and integrating circuit 33 is applied; and an output circuit 35 constituted by an operational amplifier OP5 for amplifying a voltage generated across the resistor Ri as a detection signal V representing an air-fuel ratio.

Thus, when the air-fuel ratio detecting circuit 30 is operated, a predetermined current flows into the oxygen concentration cell element 8 to thereby pump oxygen out of the hollow portion 9a into the porous electrode 7 side of the oxygen concentration cell element 8. A voltage, corresponding to a ratio of oxygen partial pressure at the porous electrode 7 side to the oxygen partial pressure in the hollow portion 9a, is generated between the porous electrodes 6 and 7 of the oxygen concentration cell element 8. Then, a current (a pumping current) flowing in the oxygen pumping element 4 is bidirectionally controlled in the air-fuel ratio detecting circuit 30 so that the voltage generated between the porous electrodes 6 and 7 of the oxygen concentration cell element 8 becomes a predetermined value determined by the reference voltage. That is, the oxygen partial pressure in the hollow portion 9a becomes fixed, and the current value is produced as the detection signal V.

In short, the current flowing in the oxygen pumping element 4 is controlled in direction such that oxygen is pumped out of the measuring gas into the hollow portion 9a when the oxygen partial pressure in the hollow portion 9a is lower than a predetermined value, while oxygen is discharged out of the hollow portion 9a into a surrounding measuring gas when the oxygen partial pressure in the hollow portion 9a is higher than a predetermined value. In this manner, the oxygen partial pressure in the hollow portion 9a is kept fixed and a detection signal V, which varies continuously, extending from a rich region to a lean region, of an air-fuel ratio can be obtained.

In the thus arranged air-fuel ratio sensors, however, there is a problem that the detection signal may fluctuate depending on the temperature and pressure of the measuring gas, and the air-fuel ratio sensor may be deteriorated by the measuring gas through long time use so as allow the detection characteristics thereof to vary.

Experiments were conducted where a plurality of air-fuel ratio sensors of this embodiment were produced, differing only in arrangement of the gas-diffusion limiting layer 20. The experiment determined the pumping current IP flowing in the oxygen pumping element 4 on the basis of the detection signal obtained by using the air-fuel ratio detecting circuit 30 to thereby obtain the temperature dependence, pressure dependence, and response of those air-fuel ratio sensors (Experiment 1).

Next, a selected one of the foregoing air-fuel ratio sensors was confirmed, on the basis of the results of Experiment 1, that the temperature dependence and the pressure dependence thereof was less than a predetermined level. The selected sensor was mounted on an actual internal combustion engine, and the dependence of the air-fuel ratio sensor on the running condition of the internal combustion engine was determined while changing the running condition of the internal combustion engine (Experiment 2).

Further, a plurality of air-fuel ratio sensors were produced, exactly like the foregoing air-fuel ratio sensor and confirmed, on the basis of the results of Experiment 1, that the temperature dependence and the pressure dependence thereof were less than a predetermined level. The deposit-resistance property of each of the produced air-fuel ratio sensors was determined through endurance tests by use of an internal combustion engine using lead containing gasoline as fuel (Experiment 3).

Description will be made hereunder as to those experiments and the results thereof.

EXPERIMENT 1

In order to perform this experiment, for each air-fuel ratio sensor, detection element layers constituting the oxygen pumping element 4 and the oxygen concentration cell elements 8 were formed through the following procedure. That is, 5.5 mole percent of yttrium oxide was added to and mixed with zirconia oxide. The mixture was subject to roast-sintering reaction, and then ground into powder. The powder was mixed with an organic binder and an organic solvent so as to be formed into green sheets each having a thickness of about 0.4 mm, and platinum electrodes were printed on those sheets to thereby obtain the detection element layers. The spacer 9, to be laminated between the detection elements, was made of zirconia. Paste, which was made of alumina powder having particle size distribution of 0.1–5 $\mu$m and a mean particle size of 1.5 $\mu$m and to which $SiO_2$ was added as a flux portion by 0–8.5 weight percent, was printed in each notch portion of the spacer 9 to thereby form the gas-diffusion limiting layer 20. The shield 10 of zirconia was further laminated on the lamination of the detection element, and the resultant lamination was burnt. Through the process described above, seven air-fuel ratio sensors S1 through S7 were produced, each having a shape of the size as shown in Table 1 and being different in arrangement of the gas-diffusion limiting layer from each other, as shown Table 2.

The heating elements 15 and 16 were formed such that Green sheets containing alumina as a main component were produced, heating resistor patterns were printed on the green sheets, and then the green sheets were brunt. The thus burnt sheets carrying the heating resistor patterns were laminated respectively on the opposite side surfaces of the foregoing burnt lamination of the detection elements through heat-resistant cement forming the spacers 11 and 12. In this embodiment, the thickness of each of the spacers 11 and 12 was made to be 100 $\mu$m.

Since the porous electrode 2 is made to be in direct contact with a measuring gas, a porous layer of alumina was formed on the surface of the porous electrode 2. Further, the thickness of the gas-diffusion limiting layer, shown in Table 2, represents the depth of a measuring gas in the diffusion direction, that is, a path length when the measuring gas passes through the gas-diffusion limiting layer, and is represented by W in FIG. 2. In this embodiment, the width of the gas-diffusion limiting layer, that is, the width of the notch portion shown by X in FIG. 2, was made to be 1 mm.

TABLE 1

|  | Size (thickness × width × length) | Main components |
|---|---|---|
| Solid electrolytic (1, 5) | 1.2 mm × 4 mm × 45 mm | $Y_2O_3$—$ZrO_2$ |
| Porous electrode 2, 3, 6, 7 | 20 $\mu$m × 2 mm × 7 mm | Pt + $Y_2O_3$—$ZrO_2$ |
| Sapcer (9) including gas-diffusion limiting layer and hollow portion | 80 $\mu$m × 4 mm × 45 mm | $Al_2O_3$ |
| Hollow portion i.e., Measuring gas chamber (9a) | 40 $\mu$m × 2.0 mm × 7.7 mm | — |
| Shield (10) | 0.35 mm × 4 mm × 45 mm | $Y_2O_3$—$ZrO_2$ |

TABLE 2

| A/F Sensor | Burning Temperature (°C.) | Flux quantity (%) | Porosity (%) | Mean pore size ($\mu$m) | Pore diameter distribution ($\mu$m) | Thickness of gas diffusion limit layer ($\mu$m) | (1) Temperature dependence (%) | (2) Pressure dependence (%) | (3) Response (mscc) |
|---|---|---|---|---|---|---|---|---|---|
| S1 | 1500 | 8.5 | 8.8 | 0.5 | 0.1–1.5 | 700–750 | +1.5 | +12 | 515 ± 50 |
| S2 | 1500 | 4.0 | 10.3 | 1.7 | 0.1–2.5 | 700–750 | +4.2 | +8.1 | 345 ± 50 |
| S3 | 1500 | 0 | 15.5 | 2.0 | 0.1–4.5 | 200–500 | +6.5 | +7.7 | 297 ± 50 |
| S4 | 1500 | 0 | 20.1 | 2.3 | 0.1–5.5 | 700–750 | +4.3 | +6.5 | 315 ± 50 |
| S5 | 1500 | 0 | 25.8 | 2.3 | 0.1–5.5 | 500–800 | +3.7 | +7.9 | 253 ± 50 |
| S6 | 1480 | 0 | 29.3 | 2.7 | 0.1–7.0 | 700–900 | +8.7 | +5.4 | 265 ± 50 |
| S7 | 1470 | 0 | 32.2 | 3.5 | 0.1–7.0 | 700–900 | +17 | +3.6 | 245 ± 50 |

In the first stage of Experiment 1, the thus formed air-fuel ratio sensors S1 through S7 were arranged in an atmosphere of predetermined pressure in which a nitrogen gas and an oxygen gas were mixed with each other with a predetermined ratio, and the temperature dependence of the air-fuel ratio sensors was measured while changing the temperature of the detection element portion by changing the voltage applied to the heating elements 15 and 16.

The results have provided that the pumping current Ip varied as shown by (1) in Table 2 when the temperature of the detection element portion varied by 100° C., and that the smaller the porosity and the pore size of the gas-diffusion limiting layer 20, the lower the temperature dependence of the air-fuel ratio sensors could be made. This is because the smaller the porosity and the pore size of the gas-diffusion limiting layer 20, the larger the fine pore diffusion when a measuring gas passes through the gas-diffusion limiting layer 20 becomes.

In the second stage of Experiment 1, the voltage applied to the heating elements 15 and 16, and the ratio of the nitrogen gas to the oxygen gas in the surrounding atmosphere were kept fixed, and the pressure dependence of the air-fuel ratio sensors was measured while changing the pressure of the surrounding atmosphere.

The results proved that the pumping current Ip varied as shown by (2) in Table 2 when the pressure of the surrounding atmosphere was changed by 0.3 atm, and that the larger the porosity and the pore size, the lower the pressure dependence of the air-fuel ratio sensors could be made. This is because, converse to the foregoing temperature dependence, the larger the porosity and pore size of the gas-diffusion limiting layer 20, the larger the ratio of the molecular diffusion when a measuring gas passes through the gas-diffusion limiting layer 20 becomes.

In the third stage of Experiment 1, each of the air-fuel ratio sensors was mounted on an actual internal combustion engine, and measurement was made with respect to the response of the detection signal when an air-fuel ratio was changed from 12 to 18 in the state where the internal combustion engine was being rotated at 1500 r.p.m. The results provided that when the air-fuel ratio of the internal combustion engine was changed from 12 to 18, the time taken for the detection signal to change 10%–90% was as shown by (3) in Table 2, and that the smaller the pore size and the porosity were made, the lower the response became. This is because the smaller the porosity and the pore size, the lower the diffusion speed of the measuring gas in the gas-diffusion limiting layer 20.

The results of the foregoing experiments have proved that the air-fuel ratio sensor, in which the temperature dependence and the pressure dependence were kept within 10%, includes the air-fuel ratio sensors S2 through S6 having porosity within a range of from 10% to 30%, a pore size within a range of from 0.1 μm to 7.0 μm, and a mean pore size within a range of from 1.0 μm to 3.0 μm. Therefore it will suffice to arrange the gas-diffusion limiting layer 20 to make the porosity and the mean pore size be within those ranges as described above. Further, it has been provided that, of all the air-fuel ratio sensors, the temperature dependence and the pressure dependence can be suppressed within 8% in the air-fuel ratio sensors S3 through S5 having porosity within a range of from 15% to 25%, and therefore in order to obtain a more stable detection signal, it will suffice to arrange the gas-diffusion limiting layer 20 to have porosity within the range described above.

EXPERIMENT 2

Figure 4:
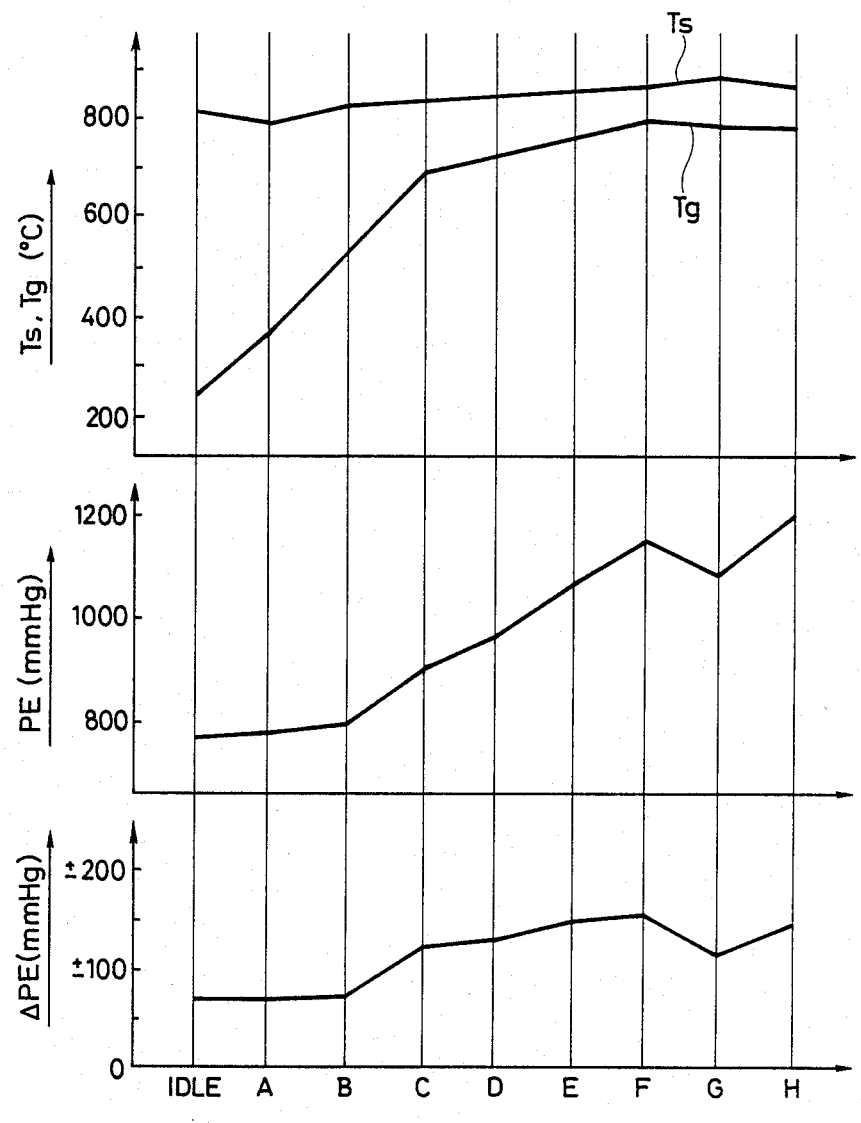
FIG. 4 is a diagram showing the running state of an internal combustion engine when Experiment 2 was carried out and a change of the temperature of the air-fuel ratio sensor.
Figure 5:
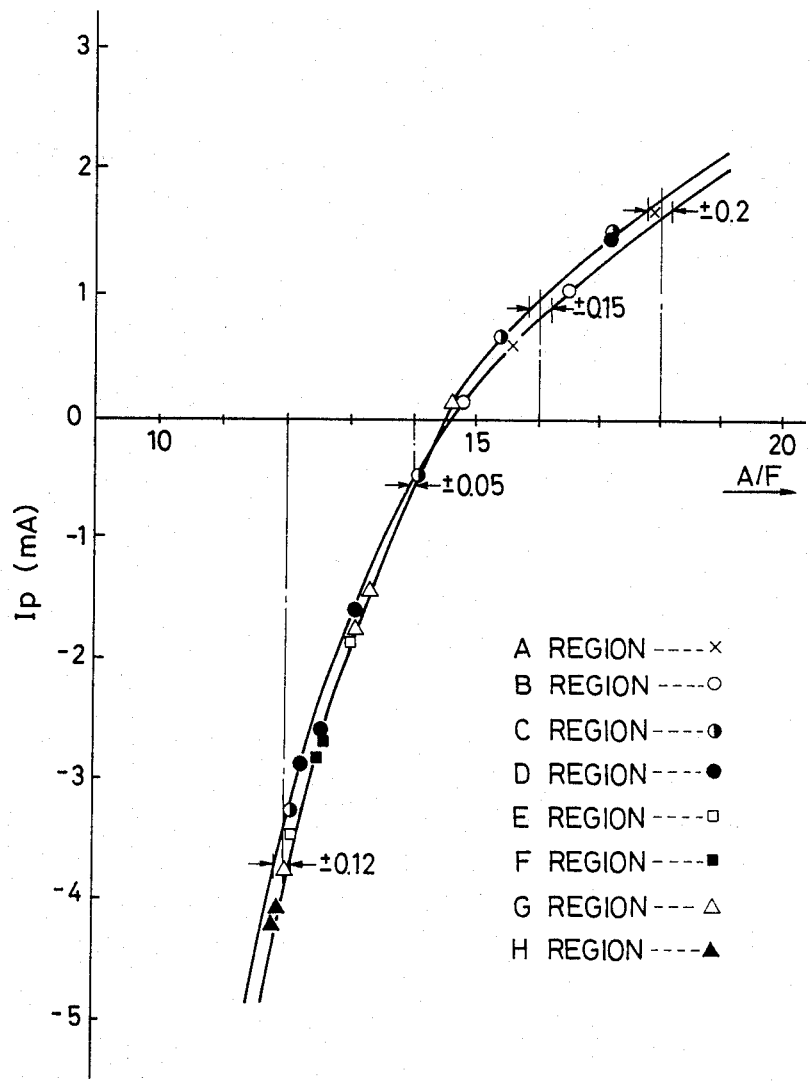
FIG. 5 is a diagram showing the results of Experiment 2.

The air-fuel ratio sensor S5 having porosity of 25.8%, a mean pore size of 2.3 μm, and a thickness of 500–800 μm, which was confirmed, on the basis of the results of the Experiment 1, to have satisfactory temperature dependence and pressure dependence, was attached to an exhaust gas system of a 6-cylinder gasoline engine having a 200 c.c. piston capacity, and the detection signal was measured in the running regions A through H shown in Table 3. FIG. 4 shows the results of measurement of the exhaust gas temperature Tg, the detection element temperature Ts, the exhaust gas pressure PE, and the quantity of change of exhaust gas pressure (pulsation of exhaust gas) PE in idling and in running in the regions A through H. FIG. 5 shows the results of measurement of the pumping current.

TABLE 3

| Running Region | Engine Speed (r.p.m.) | Engine Load Pb or S | Engine Output Region (PS) |
|---|---|---|---|
| A | 1750 | Pb: −400 | 10 |
| B | 3500 | Pb: −400 | 18 |
| C | 3500 | Pb: −100 | 57 |

TABLE 3-continued

| Running Region | Engine Speed (r.p.m.) | Engine Load Pb or S | Engine Output Region (PS) |
|---|---|---|---|
| D | 3500 | S: Full open | 69 |
| E | 4000 | S: Full open | 78 |
| F | 4500 | S: Full open | 83 |
| G | 5000 | S: 4/5 | 72 |
| H | 5000 | S: Full open | 90 |

(Pb and S represents the intake pressure and the throttle opening respectively.)

In a actual combustion equipment (in this experiment, an internal combustion engine) to which an air-fuel ratio sensor is attached, not only the exhaust gas temperature and the exhaust gas pressure fluctuate in accordance with the running condition of the combustion equipment but also the exhaust gas pressure always pulsates. However, it has been found that, as seen from FIG. 4, if the air-fuel ratio sensor S5 was used, the fluctuation width of the detection signal with respect to the synthetic air-fuel ratio can be suppressed within 2.5% calculated in terms of air-fuel ration in the range of from 12 to 18 of the air-fuel ration.

That is, as shown in FIG. 5, the fluctuation width of the pumping current Ip in the running regions in which the air-fuel ratio become 18, 16, 14, and 12 was ±0.2, ±0.15, ±0.05, and ±0.12, respectively, calculated in terms of air-fuel ratio. The results show that the output fluctuation of the detection signal obtained by the air-fuel ratio sensor S5 is substantially within 10%. It has been confirmed by this Experiment 2 that if the air-fuel ratio sensor S5 is used, the air-fuel ratio can be stably detected even if the running condition of an actual internal combustion engine fluctuates.

Further, the same measurement was performed with respect to the other air-fuel ratio sensors S2, S3, S4, and S6 which was confirmed by the foregoing Experiment 1 that both the temperature dependence and the pressure dependence was satisfactory, and as a result of the measurement it was confirmed that the fluctuation width of the detection signal with respect to the running fluctuation of the internal combustion engine was kept within 2.5% calculated in terms of air-fuel ratio.

EXPERIMENT 3

In order to perform this experiment, a plurality of air-fuel ratio sensors (that is, air-fuel sensors according to the present invention) were produced exactly like the foregoing air-fuel ratio sensors which were confirmed, on the basis of the results of Experiment 1, that both the temperature dependence and the pressure dependence thereof were good, and which were provided with a gas-diffusion limiting layer having porosity within a range of from 10% to 30%, a mean pore size of 1.0 μm–3.0 μm, and a thickness of 200 μm–1000 μm. 4-cylinder gasoline engines of 1600 c.c. piston capacity were used.

Figure 6:
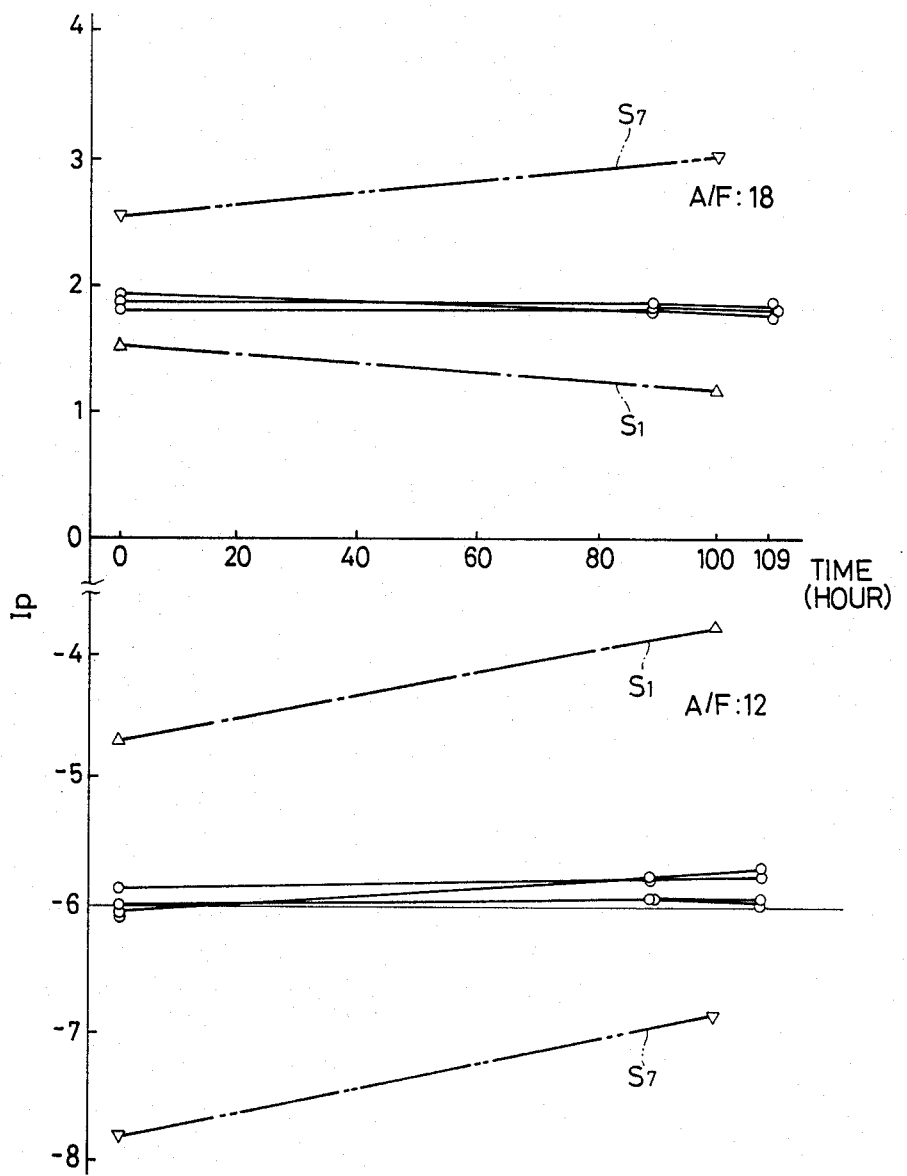
FIG. 6 is a diagram showing the results of Experiment 3.
Figure 7:
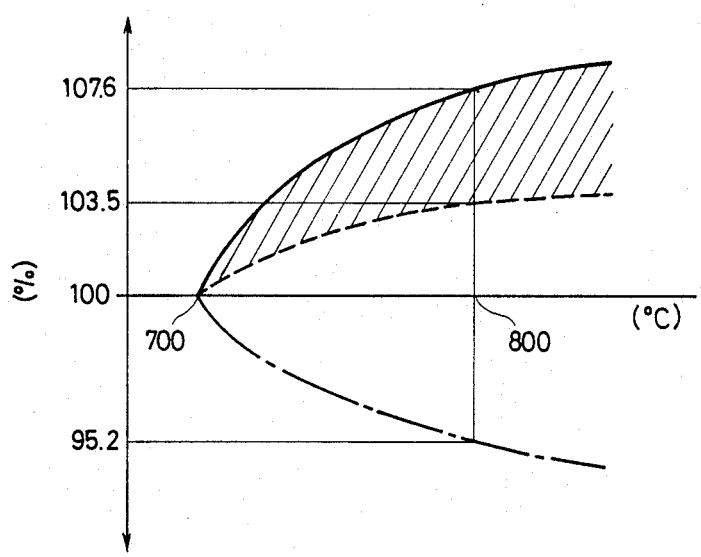
FIG. 7 is a diagram showing a fluctuation of the air-fuel ratio detection signal against a change of the temperature of the detection element, which is the theoretically obtained by the expression representing the molecular diffusion and the fine pore diffusion.
Figure 8:
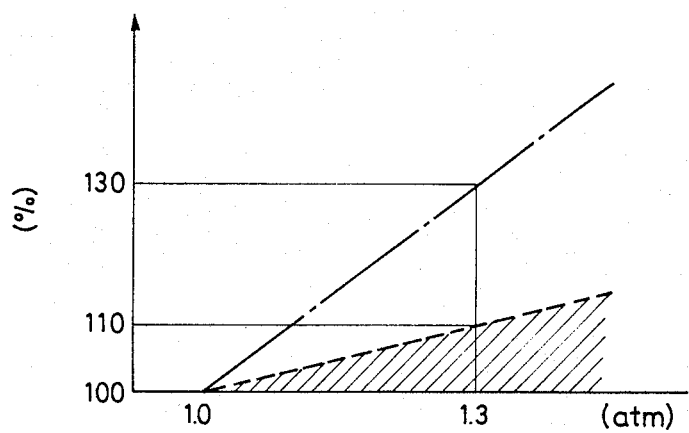
FIG. 8 is a diagram showing a fluctuation of the air-fuel ratio detection signal against a change of pressure of the measuring gas, which is theoretically obtained by the expression representing the molecular diffusion and the fine pore diffusion.

In the first stage of Experiment 3, of the thus prepared air-fuel sensors, each of four air-fuel ratio sensors was attached to an exhaust gas system of the foregoing engine, and the engine was driven for 109 hours under the following predetermined conditions. That is, fuel: gasoline containing lead (containing lead by 1.5 g/Gal); an air-fuel ratio: about 12; and rotational speed: 500 r.p.m.; to thereby perform an endurance test of those four air-fuel ratio sensors. As shown in FIG. 6, the fluctuation width of the pumping current Ip after the endurance test, calculated in terms of air-fuel ratio, was −0.15 at the maximum and −0.075 on an average at the air-fuel ratio of 12, and was +0.13 at the maximum and +0.005 on an average at the air-fuel ratio of 18.

It has been found by the above Experiment 3 that even in an internal combustion engine using lead-containing gasoline which causes a problem of deterioration of an air-fuel ratio sensor due to deposits in exhaust gas, if the foregoing air-fuel ratio sensor is used, the fluctuation of the detection signal can be reduced (the mean value of the fluctuation width of the detection signal in the first stage of Experiment 3 was suppressed to about 3%) and sufficient durability can be obtained. This is because the porosity and the pore size of the gas-diffusion limiting layer is set to the size, as described above, to thereby make it possible to reduce blockage due to deposits in the gas-diffusion limiting layer, and the thickness of the gas-diffusion limiting layer is set to the size, as described above, to thereby make it possible to prevent exhaust gas from directly hitting on the electrode layer at the hollow portion 9a side.

In the second stage of Experiment 3, each of the air-fuel ratio sensors S1 and S7, which was confirmed in the Experiment 1 that the temperature dependence or the pressure dependence was unsatisfactory, was attached to the exhaust gas system of the engine used in the foregoing first state of Experiment 3, and an endurance test was performed for 100 hours under the same running conditions as those in the first stage of Experiment 3. As indicted by one-dotted chain lines in FIG. 6, the fluctuation width of the pumping current Ip of the air-fuel ratio sensor S1 calculated in terms of air-fuel ratio was −0.75 at the air-fuel ratio of 12 and was +1.0 at the air-fuel ratio of 18. As indicated width of the pumping current Ip of the air-fuel ratio sensor S7 calculated in terms of air-fuel ratio was −0.42 at the air-fuel ratio of 12 and was −0.6 at the air-fuel ratio of 18. The results provides that sufficient durability can not be obtained in both the sensors S1 and S7. This is because in the air-fuel ratio sensor S1, the porosity and the pore size of the gas-diffusion limiting layer are so small that pores are blocked, while in the air-fuel ratio sensor S7, on the contrary, the porosity and the pore size of the gas-diffusion limiting layer are so large that the lead component in the exhaust gas is transmitted into the measuring gas chamber so that the electrode is affected by the lead component.

In the third stage of Experiment 3, alumina powder having the mean particle size of 1 μm was pressed with pressure of about 0.5 kg/cm² against the gas-diffusion limiting layer of each of two air-fuel ratio sensors of the plurality of air-fuel rate sensors prepared as described above to thereby block the pores, and change of the detection signal was measured. As a result, one detection signal did not vary and the other detection signal fluctuated by 1.5%.

Further, the same experiment was performed on the remainder air-fuel ratio sensors, and it was confirmed that the rate of change of the output signal was within 2%.

As described above in detail, in the air-fuel ratio sensor according to the present invention, not only the temperature dependence and the pressure dependence of the detection signal can be suppressed to a low level, but also the durability of the air-fuel ratio sensor can be improved. Therefore, even in the case of fluctuation of the running conditions of various combustion equipment such as an internal combustion engine or the like to which the air-fuel ratio sensor is attached, a normally stale detection signal can be obtained and the accuracy in air-fuel ratio detection can be assured for a long time.

What is claimed is:

1. An air-fuel ratio sensor for sensing a gaseous atmosphere, comprising:
    a detection element having a pair of porous electrodes on an oxygen ion-conductive solid electrolyte;
    a gas-diffusion limiting portion for limiting diffusion of the gaseous atmosphere into one of said pair of porous electrodes, said gas-diffusion limiting portion being provided such that said one of said pair of porous electrodes communicates with the gaseous atmosphere through said gas-diffusion limiting portion, said gas-diffusion limiting portion being made of porous material having a porosity, a mean pore size and a thickness in the ranges of 10%–30%, 1 μm–3 μm and 200 μm–1000 μm, respectively;
    means for applying an electric voltage of a predetermined value between said pair of porous electrodes to transfer oxygen into and out of another one of said porous electrodes, the oxygen transmission accompanying electric current through said detection element; and
    means for measuring the air/fuel ration of the gaseous atmosphere based on the current flow through said detection element.

2. An air-fuel ratio sensor of claim 1, wherein said gas-diffusion limiting portion is in direct contact with said one of said pair of porous electrodes.

3. An air-fuel ratio sensor of claim 1, wherein a hollow portion is formed between said one of said pair of porous electrodes and said gas-diffusion limiting portion.

4. An air-fuel ration sensor for sensing a gaseous atmosphere, comprising:
    a detection element having a pair of porous electrodes on an oxygen ion-conductive solid electrolyte;
    a gas-diffusion limiting portion for limiting diffusion of the gaseous atmosphere into one of said pair of porous electrodes, said gas-diffusion limiting portion being provided such that said one of said pair of porous electrodes communicates with the gaseous atmosphere through said gas-diffusion limiting portion, said gas-diffusion limiting portion being made of porous material having a porosity, a pore size and a thickness in the ranges of 15%–25%, 0.1 μm–7 μm and 400 μm–800 μm, respectively;
    means for applying an electric voltage of a predetermined value between said pair of porous electrodes to transfer oxygen into and out of another one of said pair of porous electrodes, the oxygen transmission accompanying electric current through said detection element; and
    means for measuring the air/fuel ratio of the gaseous atmosphere based on the current flow through said detection element.

5. An air-fuel ratio sensor of claim 4, wherein the porous material of said gas-diffusion limiting portion is selected from a group consisting of alumina, spinel, forsterite, and zirconia.

6. An air-fuel ratio sensor of claim 4, wherein said solid electrolyte is selected from a group consisting of a solid solution of zirconia and yttria or zirconia and calcia.

7. An air-fuel ration sensor of claim 4, wherein said porous electrodes are selected from a group consisting of platinum and rhodium.

8. An air-fuel ratio sensor for sensing a gaseous atmosphere, comprising:
   an oxygen concentration cell element having first and second porous electrodes on an oxygen ion-conductive solid electrolyte;
   an oxygen pumping element having third and fourth porous electrodes on both sides of an oxygen ion-conductive solid electrolyte;
   means for defining a gas compartment disposed between said second electrode of said oxygen concentration cell element and said third electrode of said oxygen pumping element;
   a gas-diffusion limiting portion for limiting the diffusion of the gaseous atmosphere into said gas compartment, said gas-diffusion limiting portion being disposed such that said gas compartment communicates with the gaseous atmosphere through said gas-diffusion limiting portion, said gas-diffusion limiting portion being formed of porous material having a porosity, a mean pore size and a thickness in the ranges of 10%–30%, 1 $\mu$m–3 $\mu$m and 200 $\mu$m–1000 $\mu$m, respectively;
   means for controlling an electric current flow through said oxygen pumping element, the current flow being controlled to pump oxygen into or out of said gas compartment so that an electric voltage between said electrodes of said oxygen concentration cell element is maintained at a predetermined value; and
   means for measuring the air/fuel ratio of the gaseous atmosphere based on the electric current flow through said oxygen pumping element as a result of said control means.

9. An air/fuel ratio sensor of claim 8, further comprising:
   means for shielding said first electrode of said oxygen concentration cell element from the gaseous atmosphere; and
   means for allowing oxygen to leak from said first electrode into the gas compartment;
   whereby said first electrode acts as an inner reference oxygen source for collecting oxygen extracted at said second electrode from said gas compartment.

10. An air-fuel ratio sensor of claim 9, wherein said oxygen leak allowing means comprises a porous insulator and a through hole connected between said first and second electrodes of said oxygen concentration cell element.

11. An air-fuel ratio sensor of claim 9, further comprising means for causing a predetermined amount of current to flow through said oxygen concentration cell element so that oxygen from the gas compartment is transferred to said first electrode of said oxygen concentration cell element.

12. An air-fuel ratio sensor of claim 8, wherein the porous material of said gas-diffusion limiting portion is selected from a group consisting of alumina, spinel, forsterite, and zirconia.

13. An air-fuel ratio sensor of claim 8, wherein said solid electrolyte is selected from a group consisting of a solid solution of zirconia and yttria or zirconia and calcia.

14. An air-fuel ratio sensor of claim 8, wherein said porous electrodes are selected from a group consisting of platinum and rhodium.

15. An air-fuel ratio sensor for sensing a gaseous atmosphere, comprising:
   an oxygen concentration cell element having first and second porous electrodes on an oxygen ion-conductive solid electrolyte;
   an oxygen pumping element having third and fourth porous electrodes on both sides of an oxygen ion-conductive solid electrolyte;
   means for defining a gas compartment disposed between said second electrode of said oxygen concentration cell element and said third electrode of said oxygen pumping element;
   a gas-diffusion limiting portion for limiting the diffusion of the gaseous atmosphere into said gas compartment, said gas-diffusion limiting portion being disposed such that said gas compartment communicates with the gaseous atmosphere through said gas-diffusion limiting portion, said gas-diffusion limiting portion being formed of porous material having a porosity, a pore size and a thickness in the ranges of 15%–25%, 0.1 $\mu$m–7 $\mu$m and 400 $\mu$m–800 $\mu$m, respectively;
   means for controlling an electric current flow through said oxygen pumping element, the current flow being controlled to pump oxygen into or out of said gas compartment so that an electric voltage between said electrodes of said oxygen concentration cell element is held at a predetermined value; and
   means for measuring the air/fuel ratio of the gaseous atmosphere based on the electric current flow through said oxygen pumping element as a result of said control means.

* * * * *